United States Patent [19]

Pitzele et al.

[11] Patent Number: 4,533,739

[45] Date of Patent: Aug. 6, 1985

[54] 2-[(AMINOPHENYL AND AMIDOPHENYL)AMINO]-1-AZACYCLOALKANES HAVING ANTIDIARRHEAL ACTIVITY

[75] Inventors: Barnett S. Pitzele, Skokie; Stella S. T. Yu, Morton Grove; Robert W. Hamilton, Wilmette; Alan E. Moormann, Skokie, all of Ill.

[73] Assignee: G. D. Searle & Co., Skokie, Ill.

[21] Appl. No.: 433,922

[22] Filed: Oct. 12, 1982

[51] Int. Cl.$^3$ ............................................ C07D 207/18
[52] U.S. Cl. ..................................... 548/559; 548/218; 548/476; 564/92; 564/305; 546/224; 514/867
[58] Field of Search .......................................... 548/559

[56] References Cited

U.S. PATENT DOCUMENTS 3,563,994  2/1971  Wollweber et al. ................. 546/223
3,769,274  10/1973  Wollweber et al. ............ 260/239 B
3,772,330  11/1973  Enders et al. ........................ 548/559

OTHER PUBLICATIONS

C. J. Niemegeers, F. M. Lennerts, and P. A. Janssen, "Diphenoxin, the Active Ingredient of Diphenoxylate", *Arzneim-Forsch.*, 22, 516–518, (1972).

H. J. Binder, "Net Fluid and Electrolyte Secretion . . . ", in *Mechanisms of Intestinal Secretion*, edited by H. J. Binder, New York: Alan R. Liss, 1979, pp. 1–16.

H. I. Jacoby and C. H. Marshall, "Antagonism of Cholera Enterotoxin by Anti-Inflammatory Agents in the Rat", *Nature*, (London), 235, 163–165, (1972).

R. A. Fisher, "Principles of Statistical Estimation", in *Statistical Methods for Research Workers*, 14th edn., Hafner, New York, pp. 301–339.

J. Berkson, "A Statistically Precise and Relatively Simple Method of Estimating the Bioassay with Quantal Response on Logistic Function", *J. Am. Stat. Assn.*, 48, 565–599, (1953).

*Primary Examiner*—Alan L. Rotman
*Attorney, Agent, or Firm*—John J. McDonnell

[57] ABSTRACT

This invention relates to the novel use of certain aromatic substituted amidines as antidiarrheals.

4 Claims, No Drawings

2-[(AMINOPHENYL AND AMIDOPHENYL)AMINO]-1-AZACYCLOALKANES HAVING ANTIDIARRHEAL ACTIVITY

BACKGROUND OF THE INVENTION (a) Field of the Invention

This invention relates to novel and known aromatic substituted cyclic amidines. In particular, one aspect of the invention relates to a method useful in the treatment of diarrhea. In another aspect of the invention, it relates to novel compounds useful in the treatment of diarrhea.

Diarrhea is a condition in which an abnormally frequent discharge of liquid or semi-liquid material from the bowel is present. The consistency of the normal discharge from the intestine is that of a semi-solid; the frequency of discharge varies but is usually not more than twice in 24 hours. When the stool is more like a liquid and must be discharged three or more times a day, the condition of diarrhea exists. Diarrhea may be caused by the eating of indigestible or irritable foods, or food to which the individual is allergic. It may also be caused by infection or by nervousness, which causes the intestine to discharge before the content can assume its normal form. Too much roughage, taken as a means of relieving constipation, may bring on diarrhea. Bran, cabbage and other fibrous food are often the cause. Lastly, many drugs, notably antibiotics, are known to cause diarrhea as a side effect.

Currently, mild diarrhea has been treated with binding agents such an aluminum hydroxide gel, kaolin, pectin and bismuth. More serious diarrhea has been treated with opiates which act by increasing segmenting activity. Diphenoxylate (a synthetic derivative), tincture of opium, and camphorated tincture of opium (paregoric) are effectively used. However, all the problems associated with opiates exist, and the compounds merely treat symptoms not etiology, and therefore may lead to complication and even death if care is not taken.

(b) Prior Art

Cyclic phenylamidines, such as 2-(3,4-dichlorophenylimino)-N-methylpyrrolidine, are known (U.S. Pat. No. 3,189,648). Furthermore, pharmacodynamically active phenylcycloamidines are known, such as 2-(2,6-dichloroophenylimino)pyrrolidine (Netherlands patent specification No. 6805573). In these compounds, however, the pharmacodynamic activities, such as lowering of blood pressure, hyperglycemic activity and inhibitory action on the central nervous system, are specifically linked to the ortho-substitution of the phenyl nucleus.

Other 2-phenyliminopyrrolines substituted in the meta- and para-positions, for example by chlorine or other halogen atoms, or by an alkyl, nitro or alkoxy group, are pharmacodynamically inactive.

Lastly, the known compounds useful in the method aspect of the invention are described in U.S. Pat. No. 3,769,274. These compounds are described as parasiticides and hypotensive agents.

SUMMARY OF THE INVENTION

It has been discovered, therefore, that the following compounds are useful as antidiarrheals, which act by decreasing aqueous secretion in the intestines. The compounds do not exhibit the problems associated with opiates and since they act at the source of the condition rather than symtomatologically, the associated complications may be eliminated.

A compound of the formula:

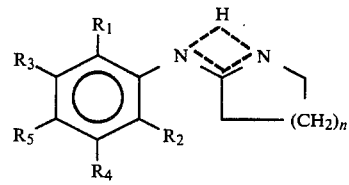

III wherein $R_1$, $R_2$, and $R_3$ each being the same or different are:
 (a) hydrogen;
 (b) alkyl of 1 to 6 carbon atoms, inclusive; or
 (c) halogen;
with the proviso that $R_1$ and $R_2$ are not hydrogen at the same time;
wherein one of $R_4$ and $R_5$ is hydrogen, alkyl of 1 to 6 carbon atoms, inclusive, or halogen and the other is of the formula: $-NR_6R_7$
wherein $R_6$ and $R_7$, each being the same or different, are:
 (a) hydrogen;
 (b) alkyl of 1 to 6 carbon atoms, inclusive;
 (c) alkoxycarbonyl of 2 to 7 carbon atoms, inclusive;
 (d) aryloxycarbonyl of 6 to 12 carbon atoms inclusive;
 (e) alkylcarbonyl of 2 to 7 carbon atoms inclusive;
 (f) arylcarbonyl of 6 to 12 carbon atoms, inclusive;
 (g) hydroxyalkoxycarbonyl of 3 to 7 carbon atoms, inclusive;
 (h) wherein $R_6$ and $R_7$ are taken together to form
  (1) $-(CH_2)_p-$; wherein p is 4 or 5;
  (2) $-(CH_2)_mCO-$, wherein m is 3 or 4;
 (i) Haloalkylcarbonyl of 2 to 7 carbon atoms, inclusive;
wherein n is an integer of from 1 to 3, inclusive; or the pharmacologically acceptable salts; the compounds being either hydrated or unhydrated.

Examples of alkyl of 1 to 6 carbon atoms inclusive are methyl, ethyl, propyl, butyl, pentyl, hexyl and the isomeric forms thereof.

Examples of halogen are bromine, iodine and chlorine.

Examples of alkoxycarbonyl of 2 to 7 carbon atoms, inclusive are methoxycarbonyl, ethoxycarbonyl, propoxycarbonyl, butoxycarbonyl, pentoxycarbonyl, hexoxycarbonyl and the isomeric forms thereof.

Examples of aryloxycarbonyl of 6 to 12 carbon atoms inclusive are phenoxycarbonyl, naphthyloxycarbonyl, and aryl substituted by for example, alkyl, halogen, or nitro groups.

Examples of alkylcarbonyl of 2 to 7 carbon atoms inclusive are acetyl, propanoyl, butanoyl, pentanoyl, hexanoyl, heptanoyl and the isomeric forms thereof.

Examples of arylcarbonyl of 6 to 12 carbon atoms, inclusive are benzoyl, naphthoyl, nicotinoyl, which can be optionally substituted by for example, alkyl, halogen, or nitro groups.

Examples of hydroxyalkoxycarbonyl of 3 to 7 carbon atoms, inclusive are hydroxyethoxycarbonyl, hydroxypropoxycarbonyl, hydroxybutoxycarbonyl, hydroxypentoxycarbonyl, hydroxhexoxycarbonyl, and the isomeric forms thereof.

The antidiarrheal activity of the compounds useful in the method aspect of the invention and the novel compounds of the invention illustrated in the examples, were tested by the following method.

Cholera-induced Intestinal Fluid Secretion

Excessive fluid secretion into the intestinal lumen is a major component of diarrhea. In order to determine the effect of the test compounds on intestinal fluid movements, the rat cholera secretion model was used. Female Charles River rats weighing 85–100 gms with free access to water were fasted for 24 hours prior to each experiment. Under ether anesthesia, a midline incision was made and a 20 cm ligated small intestinal segment was constructed starting 3.0 cm distal to the ligament of Treitz. Each segment was injected, using a 27 gauge one-half-inch needle, with 1.0 ml of a 40 mg/ml solution of crude cholera toxin (Lot #001-Wyeth) in a 0.9% saline solution. Thrity minutes before cholera toxin was injected, test compounds were administered subcutaneously to groups of 4 rats at doses of 10 and 20 mg/Kg. Animals were sacrificed 4 hr. after injection of toxin and the fluid content and exact length of the intestinal segments measured. Fluid secretion was expressed in ml/cm of intestine.

The $ID_{50}$'s of these compounds were estimated from data on at least two doses and from at least two different experiments, by the method of maximum likelihood. Lower and upper limit values for the $ID_{50}$ between which the likelihood was more than one-twentieth of its maximum were used to define an interval of estimation, approximating a 95% confidence interval. The routine calculation does not include a test of the slope of the dose-response curve.

Castol Oil-Induced Diarrhea in Rats

Castor-oil-induced diarrhea in rats was used to determine the antidiarrheal activity of test compounds with $ID_{50}$'s less than 10 mg/kg. The method of Niemegeers et al. was used. Briefly, adult Charles River male rats weighing 180–200 g were fasted for 24 hours prior to each experiment, with free access to water. Test compounds in 0.5% methylcellulose were administered intragastrically (i.g.) one hour prior to i.g. administration of castor oil at a dose of 1.0 ml/rat. Rats were observed for the presence or absence of diarrhea at hourly intervals for eight hours after castor oil administration. $ED_{50}$'s at each hourly interval were calculated for each compound using the method of Berkson.

See e.g., (1) H. J. Binder. Net Fluid and Electrolyte Secretion: The Pathophysiological Basis for Diarrhea. In Mechanisms of Intestinal Secretion. Edited by H. J. Binder, New York: Alan R. Liss, 1979, pp 1–16; (2) H. I. Jacoby and C. H. Marshall: Antagonism of Cholera Enterotoxin by Anti-inflammatory Agents in the Rat. Nature (London) 235:163–165, 1972; (3) R. A. Fisher: Principles of Statistical Estimation. In Statistical Methods for Research Workers, 14th edn. Hafner, New York, pp. 301–339; (4) C. J. Niemegeers, F. M. Lennerts, and P. A. Janssen: Diphenoxin, the Active Metabolite of Diphenoxylate. Arzneim-Forsch. 22:516–518, 1972; and (5) J. Berkson: A Statistically Precise and Relatively Simple Method of Estimating the Bioassay with Quantal Response Based on Logistic Function. J. Am. Stat. Assn. 48:565–599, 1953.

By virtue of the antidiarrheal activity, the compounds of Formula III are useful in treating diarrhea in mammals. A physician or veterinarian of ordinary skill could readily determine a subject who exhibits diarrhea.

Regardless of the route of administration selected, the compounds useful in the method aspect of the present invention and the novel compounds of the invention are formulated into pharmaceutically acceptable dosage forms by conventional methods known to the pharmaceutical art.

The compounds can be administered in such oral unit dosage forms as tablets, capsules, pills, powders, or granules. They also may be administered intraperitoneally, subcutaneously, or intramuscularly, using forms known to the pharmaceutical art. In general, the preferred form of administration is oral. An effective but non-toxic quantity of the compound is employed in treatment. The dosage regimen for preventing or treating diarrhea by the compounds of this invention is selected in accordance with a variety of factors including the type, age, weight, sex, and medical condition of the patient, the severity of the diarrhea, the route of administration and the particular compound employed. An ordinarily skilled physician or veterinarian will readily determine and prescribe the effective amount of the antidiarrheal agent required to prevent or arrest the progress of the condition. In so proceeding, the physician or veterinarian could employ relatively low dosages at first, subsequently increasing the dose until a maximum response is obtained. Dosages of the compounds of the invention are ordinarily in the area of 0.01 to 1.0 mg/kg up to about 100 mg/kg orally.

The compounds can also be administered as pharmacologically acceptable acid addition salts such as the hydrochloride, hydrobromide, hydroiodide, sulfate, phosphate, acetate, propionate, lactate, maleate, malate, succinate, tartrate and the like. Additionally, the compounds may be administered in a suitable hydrated form.

The compounds used in the method aspect of this invention and the novel compounds of the invention are prepared from variously substituted aniline derivatives and 2-activated azacycloalk-1-enes using sequences of reactions based on the general scheme of Chart A. Lactams of Formula I are converted to corresponding 2-haloazacycloalk-1-enes, Formula II, for example by reaction with active halogen compounds, such as a phosphorus oxyhalide and thionyl halide, in unreactive organic solvents, such as acetonitrile, dichloromethane, and toluene. Preferred reaction conditions employ phosphorus oxychloride in acetonitile or toluene. Compounds of Formula II are not isolated, but are allowed to react in situ with aniline derivatives, Formula III, to form compounds of Formula IV. The structures of the initially formed compounds, IV, can be elaborated using various methods, including those illustrated in the succeeding Charts.

Appropriate aniline derivatives which are not available commercially may be prepared by any number of methods known to those skilled in the art. One method for preparing appropriate anilines is illustrated in Chart B. Substituted anilines of Formula XI are protected by reaction with various sulfonyl blocking reagents, such as p-toluenesulfonyl chloride. The resultant compounds, XII, are nitrated by any of a number of methods known to those skilled in the art. A preferred method employs sodium nitrate in an aqueous mixture of acetic acid and nitric acid. The protected nitroanilines thus formed are deblocked under strongly acidic conditions, such as afforded by 90% sulfuric acid, to give compounds of Formula XIV. Addition of the nitroanilines, XIV, to a solution of one of the compounds of Formula II (Chart A, discussed above) affords intermediates, XV. Amino compounds of Formula XVI are prepared from intermediates XV by reduction. A preferred method of reduction is catalytic hydrogenation, using for example palladium or platinum on carbon as catalyst. The hydrogenations typically employ as solvent acetic acid or various alcohols, such as methanol and ethanol, which may (optionally) be acidified with hydrogen chloride.

Corresponding acylamino analogs of XVI are prepared by several methods. Direct acylation, as illustrated in Chart C, affords compounds of Formulas XXII and XXIII. An amino compound of Formula XXI can be acylated with alkanoyl halides and alkanoic anhydrides, such as acetyl chloride, propanoyl chloride, acetic anhydride, and propanoic anhydride, to corresponding alkanoyl compounds XXII. Similarly, compounds XXI can be acylated with alkyl chloroformates or dialkyl dicarbonates such as ethyl chloroformate and diethyl dicarbonate, to corresponding carbamates XXIII. Acylations are performed in unreactive solvents, such as acetonitrile and dichloromethane, or in activating solvents, such as pyridine.

An alternative preparation of carbamates XXIII is illustrated in Chart D. Compounds XXI are converted to a carbamoyl chloride intermediate, XXXI, by reaction with phosgene in an inert solvent, such as acetonitrile. Immediately upon formation, compounds XXXI are converted to the carbamates XXIII by reaction with an alcohol, such as methanol, ethanol, propanol, butanol, and the like.

Another method for preparing and using appropriate anilines is illustrated in Chart E. Nitroanilines, XLI, available commercially or by methods known to those skilled in the art (e.g., Chart B), are protected as phthalimide derivatives, Formula XLII. A preferred set of conditions for preparing the phthalimides is fusion of anilines of Formula XLI with phthalic anhydride at elevated temperatures. The nitro compounds, XLII, are reduced to anilines, XLIII, by catalytic hydrogenation in appropriately acidified solvents, such as tetrahydrofuran and ethanol containing hydrogen chloride, using such catalysts as palladium or platinum on carbon. The intermediate anilines, XLIII, are converted to acyl derivative of Formula XLIV using the acylating methods described above for Charts C and D. The phthalimide group is removed from the acylated compounds, XLIV, using hydrazine in refluxing aqueous ethanol, giving various acylaminoanilines of Formula XLV. Addition of compounds XLV to a solution of one of the compounds of Formula II (Chart A, discussed above) affords desired compounds of Formula XLVI.

Corresponding alkylamino analogs of XVI are prepared by several methods, as illustrated in Charts F and G. Methyl derivatives of Formula LI (Chart F) can be prepared from compounds XXI by reaction with formaldehyde under reductive conditions, such as provided by catalytic hydrogenation or by deactivated borohydride reagents. Preferred hydrogenation conditions include reaction in aqueous base using palladium on carbon as catalyst. A preferred borohydride reagent is sodium borohydride.

Mono- and dialkylated compounds of Formula LXII, including mono- and dimethyl derivatives, can be prepared from phthalimide intermediates XLIII, as illustrated in Chart G. Using the methods discussed above and illustrated in Chart F, phthalimide precursors of Formula XLIII (See Chart E) can be converted to methyl and dimethyl derivatives LXI by reaction with formaldehyde under reductive conditions. Furthermore, compounds XLIII can be converted to alkyl and dialkyl derivatives LXI by direct alkylation using alkyl halides, such as methyl bromide, methyl iodide, and ethyl chloride, or alkyl sulfates, such as dimethyl sulfate. A preferred alkylating agent is methyl iodide. The monoalkyl compounds LXI can be further derivatized by acylation, as described above and illustrated in Charts C and D, to give compounds of Formula LXI in which $R_6$ and $R_7$ are not identical. The phthalimide blocking group can be removed from the alkylated compounds LXI using hydrazine, as described above and illustrated in Chart E. The intermediate anilines thus formed will react with activated compounds II, as in Chart A, to form compounds LXII.

The compounds are not restricted to para-(substituted amino)phenyl derivatives. For example, Novel meta-(substituted amino)phenyl compounds may readily be prepared by the same general methods, as illustrated in Chart H. 3-Nitroanilines, Formula LXXI, will react with activated compounds II, as in Chart A, to afford nitro intermediates, LXXII. Compounds LXXII are reduced by the general methods discussed above (See Chart A.) to give meta-amino compounds of Formula LXXIII. Compounds of the Formula LXXIV can readily be prepared by the methods discussed above (See, for example, Charts C, D, F, and G). It is unexpected that these compounds are active, especially since compounds that are amino-substituted at the ortho-position are inactive.

The following examples further illustrate details for the preparation of the compounds useful in the method aspect of the invention and the novel compounds. The invention, which is set forth in the foregoing disclosure, is not to be construed or limited either in spirit or in scope by these examples. Those skilled in the art will readily understand that known variations of the conditions and processes of the following preparative procedures can be used to prepare the compounds. All temperatures are in degrees celsius unless otherwise noted.

DESCRIPTION OF THE PREFERRED EMBODIMENTS

EXAMPLE 1

2-Chloro-1-pyrroline

To a solution of 102 g (1.2 mole) of 2-pyrrolidinone in 500 ml of acetonitrile cooled in an ice-methanol bath was added dropwise a solution of 92.0 g (0.6 mole) of phosphorus oxychloride in 30 ml of acetonitrile. The reaction mixture was stirred for three hours at room temperature. The title compound thus formed was used in solution for subsequent reactions without isolation or purification.

EXAMPLE 2

2-Chloroazacyclohex-1-ene

The title compound was prepared by the method of Example 1 using 9.9 g (0.1 mole) of 2-piperidinone and used in solution without isolation or purification.

EXAMPLE 3

2-Chloroazacyclohept-1-ene

The title compound was prepared by the method of Example 1 using 122.6 g (0.2 mole) of caprolactam and used in solution without isolation or purification.

EXAMPLE 4

1-(p-Toluenesulfonamido)-2,6-dimethylbenzene

A solution of 23.4 g (0.12 mole) of 2,6-dimethylaniline and 40.5 g (0.19 mole) of p-toluenesulfonyl chloride in 75 ml of pyridine was heated at reflux for three hours. The mixture was cooled and poured into vigorously stirred 2N hydrochloric acid. The crude product was recrystallized from ethanol to give 45 g of the title compound. Structure assignment was supported by the nmr spectrum and by elemental analysis.

Calcd. for $C_{15}H_{17}NO_2S$: C, 65.43; H, 6.22; N, 5.09; S, 11.64. Found: C, 65.55; H, 6.27; N, 5.01; S, 11.81.

EXAMPLE 5

1-(p-Toluenesulfonamido)-2,6-dimethyl-4-nitrobenzene

The sulfonamide intermediate of Example 4 (6.9 g, 0.025 mole) was added to a solution of 6.3 ml of concentrated nitric acid in 50 ml of water, followed by addition of 50 ml of glacial acetic acid and 0.18 g of sodium nitrite. The mixture was heated at reflux for one hour, then poured into 100 ml of water. The crude product thus isolated was recrystallized from ethanol to give 6.5 g of the title compound. Structure assignment was supported by the nmr spectrum and by elemental analysis.

Calcd. for $C_{15}H_{16}N_2O_4S$: C, 56.24; H, 5.03; N, 8.74; S, 10.00. Found: C, 55.92; H, 4.97; N, 8.80; S, 10.14.

EXAMPLE 6

2,6-Dimethyl-4-nitroaniline

The nitrated intermediate prepared by the method of Example 5 (100 g, 0.34 mole) was stirred at room temperature in a mixture of 300 ml of sulfuric acid and 30 ml of water for one hour. The reaction mixture was poured into one liter of ice-water and the mixture made basic with ammonium hydroxide, giving the title compound (53 g). Structure assignment of the final product was confirmed by nmr spectroscopy and by elemental analysis.

Calcd. for $C_8H_{10}N_2O_2$: C, 57.82; H, 6.07; N, 16.86. Found: C, 58.10; H, 6.06; N, 16.91.

EXAMPLE 7

2,5-Dimethyl-4-nitroaniline

The title compound (31.3 g) was prepared by the methods of Examples 4, 5, and 6 using 64.3 g (0.53 mole) of 2,5-dimethylaniline. Structure assignment was supported by nmr and infrared spectra and by elemental analysis.

Calcd. for $C_8H_{10}N_2O_2$: C, 57.82; H, 6.06; N, 16.86. Found: C, 57.55; H, 6.04; N, 16.96.

EXAMPLE 8

2-[(2-Methyl-4-nitrophenyl)amino]-1-pyrroline

A mixture of 2-chloro-1-pyrroline (1.2 mole), prepared as in Example 1, and 91.3 g (0.6 mole) of 2-methyl-4-nitroaniline were heated at reflux in 900 ml of acetonitrile for two hours. The solid obtained by cooling and filtering was combined with that obtained by concentrating the filtrate to dryness, then dissolved in hot water and filtered. The solution was cooled and washed with ethyl acetate, and the aqueous phase was made basic with 4 N sodium hydroxide. The crude product was extracted into dichloromethane, which was then removed in vacuo. The resultant solid was washed repeatedly with diethyl ether to give 67.7 g of pure title compound. Structure assignment was supported by the nmr spectrum and by elemental analysis.

Calcd. for $C_{11}H_{13}N_3O_4$: C, 60.26; H, 6.00; N, 19.16. Found: C, 60.01; H, 6.00; N, 19.17.

EXAMPLE 9

2-[(2-Methyl-4-aminophenyl)amino]-1-pyrroline, dihydrochloride.

The product compound of Example 8 was dissolved in 1.2 liter of ethanol containing 53.4 ml of concentrated hydrochloric acid and hydrogenated at 2 psi over 5% palladium on carbon. After removal of catalyst by filtration, the filtrate was concentrated in vacuo to give 85 g of the title compound. Structure assignment was supported by the nmr spectrum and by elemental analysis.

Calcd. for $C_{11}H_{15}N_3.2HCl$: C, 50.39; H, 6.54; N, 16.03; Cl, 27.04. Found: C, 50.23; H, 6.51; N, 15.78; Cl, 26.68.

EXAMPLE 10

2-[(2,6-Dimethyl-4-nitrophenyl)amino]-1-pyrroline

A mixture of 2-chloro-1-pyrroline, prepared as in Example 1, and 19.9 g (0.12 mole) of the aniline product of Example 6 were heated at reflux overnight, according to the general method of Example 8. The title compound was isolated and used for subsequent reactions without further purification. Structure assignment was supported by nmr and infrared spectra.

EXAMPLE 11

2-[(2,6-Dimethyl-4-aminophenyl)amino]-1-pyrroline, dihydrochloride

The title compound was prepared by the method of Example 9 using 10.5 g of the product compound of Example 10, except that no hydrochloric acid was added during hydrogenation. The crude product was dissolved in methanol and acidified with HCl in isopropyl alcohol. Addition of diethyl ether induced precipitation of 11.6 g of the title compound. Structure assignment was supported by the nmr spectrum and by elemental analysis.

Calcd. for $C_{12}H_{17}N_3.2HCl.1/4H_2O$: C, 51.35; H, 7.01; N, 14.97; Cl, 25.26. Found: C, 51.30; H, 7.06; N, 14.69; Cl, 25.41.

EXAMPLE 12

2-[(2,5-Dimethyl-4-nitrophenyl)amino]-1-pyrroline

The title compound (9.1 g) was prepared using the method of Example 8 using 16.6 g (0.1 mole) of the aniline product of Example 7. Extractions were performed using diethyl ether rather than ethyl acetate. Structure assignment was supported by nmr and infrared spectra and by elemental analysis.

Calcd. for $C_{12}H_{15}N_3O_2$: C, 61.79; H, 6.48; N, 18.01. Found: C, 61.55; H, 6.44; N, 17.89.

EXAMPLE 13

2-[(2,5-Dimethyl-4-aminophenyl)amino]-1-pyrroline, dihydrochloride

The title compound (10.7 g) was prepared according to the method of Example 9 using 9.1 g of the product compound of Example 12. Structure assignment was supported by nmr and infrared spectra and by elemental analysis.

Calcd. for $C_{12}H_{17}N_3.2HCl.1/4H_2O$: C, 51.34; H, 7.00; N, 14.97; Cl, 25.26. Found: C, 51.51; H, 6.89; N, 14.86; Cl, 25.38.

EXAMPLE 14

2-[(2-Methyl-4-aminophenyl)amino]azacyclohex-1-ene, dihydrochloride

The title compound (8.2 g) was prepared by the methods of Examples 8 and 9 using 2-chloroazacyclohex-1-ene (0.10 mole), prepared as in Example 2, and 7.6 g (0.05 mole) of 2-methyl-4-nitroaniline. Structure assignment was supported by the nmr spectrum and by elemental analysis.

Calcd. for $C_{12}H_{17}N_3.2HCl$: C, 52.18; H, 6.93; N, 15.21; Cl, 25.67. Found: C, 52.05; H, 7.09; N, 14.92; Cl, 25.41.

EXAMPLE 15

2-[(2-Methyl-4-aminophenyl)amino]azacyclohept-1-ene, dihydrochloride

The title compound was prepared by the methods of Examples 8 and 9 using 2-chloroazacyclohept-1-ene (0.2 mole), prepared as in Example 3, and 15.2 g (0.1 mole) of 2-methyl-4-nitroaniline. Structure assignment was supported by elemental analysis.

Calcd, for $C_{13}H_{19}N_3.2HCl$: C, 50.66; H, 7.52; N, 13.63; Cl, 23.00. Found: C, 50.44; H, 7.52; N, 13.49; Cl, 22.97.

EXAMPLE 16

2-[(2-Methyl-4-acetamidopheny)amino]-1-pyrroline, hydrochloride, Method A

A mixture of 1.0 g (3.8 mmole) of the product compound of Example 9 and 30.5 mmole of acetyl chloride in 40 ml of acetonitrile was stirred at room temperature for 18 to 20 hours. The reaction mixture was then diluted eight-fold with diethyl ether. The resultant solid was collected and washed with three portions of ether, then dried in a high vacuum over 5A molecular sieves, giving the title compound as the hydrochloride salt. Structure assignment was supported by the nmr spectrum and by elemental analysis.

Calcd. for $C_{13}H_{17}N_3O.HCl.3/4H_2O$: C, 55.51; H, 6.99; N, 14.94; Cl, 12.60. Found: C, 55.41; H, 6.84; N, 14.69; Cl, 12.38.

EXAMPLE 17

2-[(2-Methyl-4-acetamidophenyl)amino]-1-pyrroline, hydrochloride, Method B

The title compound was prepared by the method of Example 16 using acetic anhydride in place of acetyl chloride. The product was identical to that prepared by Example 16.

EXAMPLE 18

2-[(2-Methyl-4-(propanamido)phenyl)amino]-1-pyrroline, hydrochloride

The title compound was prepared by the method of Example 17 using 30.5 mmole of propanoic anhydride and 1.0 g (3.8 mmole) of the product compound of Example 9. Structure assignment was supported by the nmr spectrum and by elemental analysis.

Calcd. for $C_{14}H_{19}N_3O.HCl$: C, 59.67; H, 7.15; N, 14.91; Cl, 12.58. Found: C, 60.03; H, 7.08; N, 15.04; 12.47.

EXAMPLE 19

2-[(2-Methyl-4-(chloroacetamido)phenyl)amino]-1-pyrroline, hydrochloride

The title compound was prepared by the method of Example 16 using 30.5 mmole of chloroacetyl chloride and 1.0 g (3.8 mmole) of the product compound of Example 9. Structure assignment was supported by the nmr spectrum and by elemental analysis.

Calcd. for $C_{13}H_{16}N_3OCl.HCl.1/8H_2O$: C, 51.28; H, 5.72; N, 13.80; Cl, 23.28 Found: C, 51.08; H, 5.56; N, 13.84; Cl, 23.61.

EXAMPLE 20

2-[(2-Methyl-4-(ethoxycarbonylamino)phenyl)-amino]azacyclohept-1-ene, hydrochloride The title compound was prepared by the method of Example 16 using ethyl chloroformate and 1.0 g (3.1 mmole) of the product compound of Example 15. Structure assignment was supported by the nmr spectrum and by elemental analysis.

Calcd. for $C_{16}H_{23}N_3O_2.HCl$: C, 58.98; H, 7.42; N, 12.90; Cl, 10.80. Found: C, 58.62; H, 7.37; N, 12.85; Cl, 11.04.

EXAMPLE 21

2-[(2-Methyl-4-(4-fluorobenzamido)phenyl)amino]-1-pyrroline, hydrochloride

A mixture of 1.0 g (3.8 mmole) of product compound of Example 9 and 30.5 mmole of p-fluorobenzoyl chloride in 40 ml of acetonitrile was stirred at reflux for four hours, after which time thin-layer chromatography on silica gel (9:1 ethanol/concentrated aqueous ammonia) indicated no unreacted starting amine. The reaction mixture was then diluted eight-fold with diethyl ether. The resultant solid was collected and washed with three portions of ether, then dried in a high vacuum over 5A molecular sieves, giving the title compound as the hydrochloride salt. Structure assignment was supported by the nmr spectrum and by elemental analysis.

Calcd. for $C_{18}H_{18}N_3OF.HCl$: C, 62.16; H, 5.51; N, 12.08; Cl, 10.19; F, 5.46. Found: C, 62.15; H, 5.49; N, 12.09; Cl, 10.54; F, 5.39.

EXAMPLE 22

2-[(2-Methyl-4-(butanamido)phenyl)amino]-1-pyrroline, hydrochloride

The title compound was prepared by the method of Example 21 using 30.5 mmole of butanoyl chloride and 1.0 g (3.8 mmole) of the product compound of Example 9. Structure assignment was supported by the nmr spectrum and by elemental analysis.

Calcd. for $C_{15}H_{21}N_3O.HCl.1/4H_2O$: C, 60.21; H, 7.52; N, 14.04; Cl, 11.85. Found: C, 60.21; H, 7.51; N, 13.94; Cl, 12.09.

EXAMPLE 23

2-[(2-Methyl-4-(ethoxycarbonylamino)phenyl)-amino]-1-pyrroline, hydrochloride

The title compound was prepared by the method of Example 21 using 30.5 mmole of ethyl chloroformate and 1.0 g (3.8 mmole) of the product compound of Example 9. Complete reaction, as indicated by thin-layer chromatography (See Example 21), required heating for a second day with an additional 30.5 mmole of ethyl chloroformate. Structure assignment was supported by the nmr spectrum and by elemental analysis.

Calcd. for $C_{14}H_{19}N_3O_2.HCl.1/4H_2O$: C, 55.63; H, 6.84; N, 13.90; Cl, 11.73. Found: C, 55.63; H, 6.92; N, 13.89; Cl, 11.72.

EXAMPLE 24

2-[(2-Methyl-4-(ethoxycarbonylamino)phenyl)-amino]azacyclohex-1-ene, hydrochloride The title compound was prepared by the method of Example 21 using 30.5 mmole of ethyl chloroformate and 1.0 g (3.6 mmole) of the product compound of Example 14. Structure assignment was supported by the nmr spectrum and by elemental analysis.

Calcd. for $C_{15}H_{21}N_3O_2.HCl$: C, 57.78; H, 7.11; N, 13.48; Cl, 11.37. Found: C, 57.65; H, 7.16; N, 13.63; Cl, 11.64.

EXAMPLE 25

2-[[2-Methyl-4-((1-methylethoxy)carbonylamino)-phenyl]amino]-1-pyrroline, hydrochloride To 1.2 g (4.6 mmole) of the product compound of Example 9 in 30 ml of acetonitrile was added a 10% excess of phosgene in toluene. The mixture was stirred at 20° in the absence of moisture for 16 hours, at which time a large excess (20 ml) of isopropyl alcohol was added. The reaction mixture was stirred at 20° until reaction was complete, as indicated by thin-layer chromatography on silica gel (9:1 ethanol/concentrated aqueous ammonia or 74:25:1 dichloromethane/ethanol/ammonia). The product was taken up in an eight-fold excess of diethyl ether and recovered as an oil by concentrating the extract. The title compound crystallized upon standing. Structure assignment was supported by the nmr spectrum and by elemental analysis.

Calcd. for $C_{15}H_{21}N_3O_2.HCl.1/4H_2O$: C, 56.96; H, 7.17; N, 13.28; Cl, 11.21. Found: C, 56.84; H, 7.10; N, 13.32; Cl, 11.14.

EXAMPLE 26

2-[[2-Methyl-4-((3-hydroxypropyloxy)carbonylamino)-phenyl]amino]-1-pyrroline, hydrochloride The title compound was prepared by the general method of Example 25 using the product compound of Example 9 and 1,3-propanediol. The reaction mixture was treated with an eight-fold quantity of diethyl ether, in which the product was not soluble. The oily product was triturated with several portions of ether until solid. The crude solid was stirred as a suspension in a small amount of 1:1 ethanol/methanol, and then collected by filtration. Drying in a high vacuum over 5A molecular sieves produced the desired compound as the hydrochloride salt.

Calcd. for $C_{15}H_{21}N_3O_3.HCl$: C, 54.96; H, 6.76; N, 12.82; Cl, 10.82. Found: C, 54.60; H, 6.74; N, 12.76; Cl, 10.97.

EXAMPLE 27

2-[[(2-Methyl-4-(propyloxycarbonylamino)phenyl)-amino]-1-pyrroline, hydrochloride The title compound was prepared as a crystalline solid by the method of Example 25 using the product compound of Example 9 and excess propanol. Structure assignment was supported by the nmr spectrum and by elemental analysis.

Calcd. for $C_{15}H_{21}N_3O_2.HCl.1/4H_2O$: C, 56.96; H, 7.17; N, 13.28; Cl, 11.21. Found: C, 56.84; H, 6.97; N, 13.34; Cl, 11.56.

EXAMPLE 28

2-[[2-Methyl-4-((3-methylbutyloxy)carbonylamino)-phenyl]amino]-1-pyrroline

The title compound was prepared by the general method of Example 25 using the product compound of Example 9 and excess 3-methylbutanol. The reaction mixture was filtered to remove insolubles, and the filtrate was concentrated to an oil which solidified upon trituration with hexane. The resultant impure solid was purified by low-pressure column chromatography on silica gel using as eluent ammoniacal ethanol/dichloromethane. The product was isolated as the free base. Structure assignment was supported by the nmr spectrum and by elemental analysis.

Calcd. for $C_{17}H_{25}N_3O_2.1/8H_2O$: C, 66.80; H, 8.33; N, 13.75. Found: C, 66.82; H, 8.37; N, 13.52.

EXAMPLE 29

2-[(2,6-Dimethyl-4-(ethoxycarbonylamino)phenyl)amino]-1-pyrroline, hydrochloride The title compound was prepared by the method of Example 26 using the product compound of Example 11 and excess anhydrous ethanol. Structure assignment was supported by the mmr spectrum and by elemental analysis.

Calcd. for $C_{15}H_{21}N_3O_2.HCl.3/4H_2O$: C, 55.38; H, 7.29; N, 12.92; Cl, 10.90. Found: C, 55.11; H, 7.03; N, 13.14; Cl, 11.25.

EXAMPLE 30

2-[(2-Methyl-4-(methoxycarbonylamino)-phenyl)amino]-1-pyrroline, hydrochloride

The title compound was prepared by the method of Example 26 using the product compound of Example 9 and excess methanol. The crude product was dissolved in the minimum amount of methanol and treated with diethyl ether to point of cloudiness, then cooled. Insolubles were removed by filtration and the product forced out of the filtrate by addition of ether, giving the title compound as a solid. Structure assignment was supported by the nmr spectrum and by elemental analysis.

Calcd. for $C_{13}H_{17}N_3O_2.HCl.1/4H_2O$: C. 54.17; H, 6.47; N, 14.58; Cl, 12.30. Found: C, 54.46; H, 6.27; N, 14.70; Cl, 12.65.

EXAMPLE 31

3-Methyl-4-phthalimidoaniline, hydrochloride

A mixture of 10.0 g (65.7 mmole) of 2-methyl-4-nitroaniline and 10.7 g (72.3 mmole) of phthalic anhydride was heated in an oil bath with an initial tempera- -continued

| Compound | Cholera ID$_{50}$(mg/kg)* | Castor Oil ID$_{50}$(mg/kg)-4 hr. |
|---|---|---|
| Example 14 | 13.6/26.3 | |
| Example 16 & 18 | 4.6/>100 | 3.63 |
| Example 18 | 3.1/4 | 0.97 |
| Example 19 | 7.1/>100 | |
| Example 20 | 63.4/>100 | |
| Example 21 | 41.9/>100 | |
| Example 22 | 15.4/32.8 | |
| Example 23 | 1.9/1.3 | 1.81 |
| Example 24 | 31.6/>100 | |
| Example 25 | 4.7/3.1 | |
| Example 26 | 42.7/>100 | |
| Example 27 | 55.2/>100 | |
| Example 30 | 1.9/3.0 | |
| Example 33 | 4.6/>100 | 3.63 |
| Example 39 | 6.3/10.0 | |
| Example 41 | 6.3/10.8 | |
| Example 42 & 43 | 3.4/5.0 | |
| Example 45 | 5.5/8.6 | |
| Example 46 | 8.6/14.6 | |
| Example 47 | 30.7/>100 | |

*Experimental Limits

CHART A

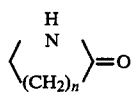  I

↓ POX$_3$ or SO$_2$X$_2$ (X = halide)

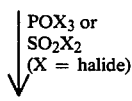  II

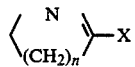

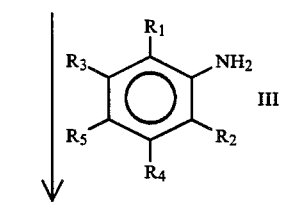  III

↓

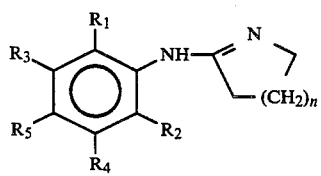  IV

CHART B

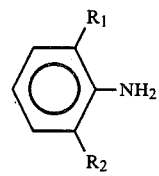  XI

↓ p-TsCl

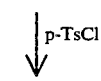  XII

↓ Nitration

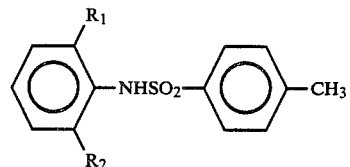  XIII

↓ (1) Acid Hydrolysis
(2) Neutralization

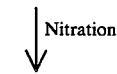  XIV

↓ II

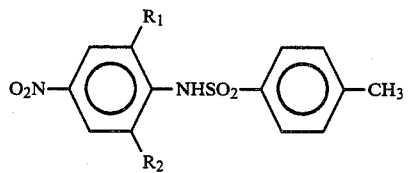  XV

↓ Reduction

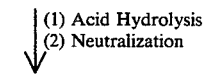  XVI

CHART C
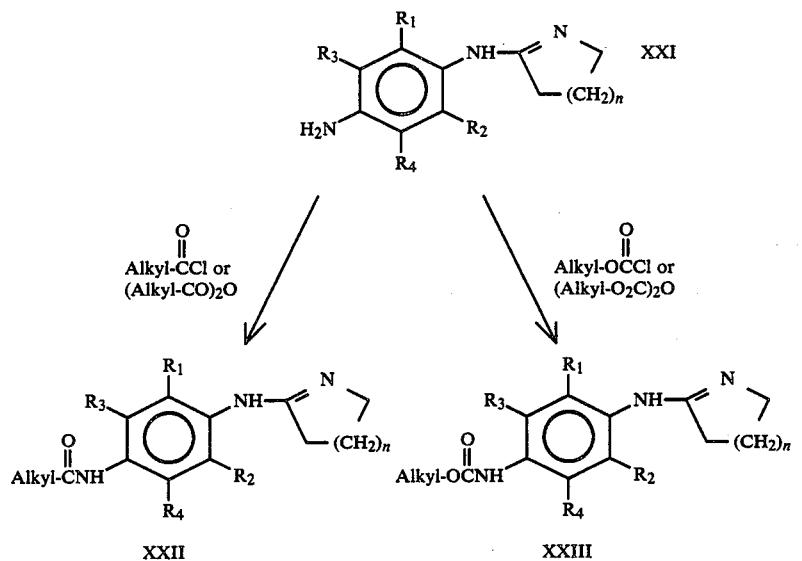
CHART D
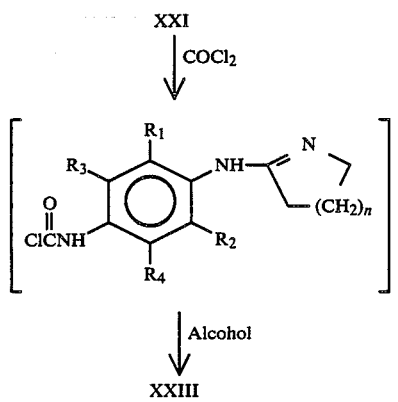
CHART E
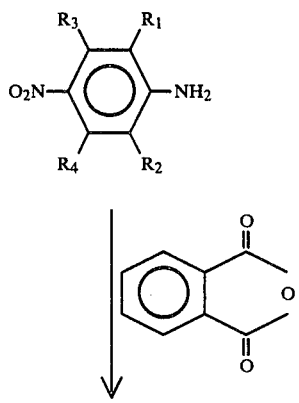
-continued
CHART E
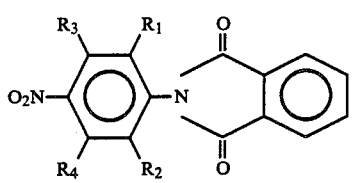
XLII
Reduction
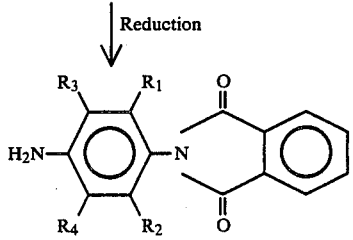
XLIII
Acylation (as Charts C,D)
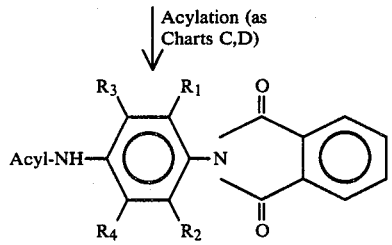
XLIV
$H_2NNH_2$ ture of 150°. As the temperature was raised slowly to 165°, the mixture melted and resolidified. The cooled mixture was triturated with 200 ml of dichloromethane and filtered, and the filtrate was washed successively with 3N aqueous hydrochloric acid, water, and 5% aqueous sodium hydroxide. The organic phase was dried over calcium chloride, treated with activated charcoal, filtered, and the filtrate concentrated in vacuo. The resultant solid was suspended in hot ethanol and, after cooling, was collected and dried, giving 15.4 g of N-(2-methyl-4-nitrophenyl)phthalimide. A portion (10.0 g) of the intermediate was hydrogenated in tetrahydrofuran containing 4 ml of concentrated aqueous hydrochloric acid using 5 psi hydrogen gas over 5% palladium on carbon. The filtered solution was concentrated to dryness and the resultant solid washed with methanol, giving 8.3 g of the title compound. The product thus isolated was used in subsequent reactions without further purification.

EXAMPLE 32

2-Methyl-4-acetamidoaniline

The product aniline of Example 31 was acetylated at room temperature using 8.2 ml (86.6 mmole) of acetic anhydride in 100 ml of pyridine. After one day the mixture was concentrated in vacuo to a syrup which afforded a solid upon trituration with water. The solid was collected, washed with water, and dried under vacuum at 40°, giving 4.8 g (16.3 mmole) of 2-phthalimido-5-acetamidotoluene. The intermediate compound was heated at reflux in 100 ml of ethanol containing 3.2 ml (65.2 mmole) of hydrazine hydrate. After 45 minutes the mixture was filtered and the filtrate was concentrated to dryness. The crude amine was used in subsequent reactions without further purification.

EXAMPLE 33

2-[(2-Methyl-4-acetamidophenyl)amino]-1-pyrroline

The product aniline of Example 32 was added to a solution of 2-chloro-1-pyrroline, prepared by the method of Example 1 using toluene, and the mixture was stirred for four hours at reflux. The solvent was removed by decanting and the residual solid was dissolved in water. The acidic solution (ca. pH 1.5) was washed with ethyl acetate and then made strongly basic (ca. pH 13) with aqueous sodium hydroxide. The crude product compound was immediately extracted into ethyl acetate. The extract was filtered and concentrated in vacuo to an oil, which solidified on standing. The solid was triturated with diethyl ether, collected, and dried under vacuum to give the title compound, the free base of the compound prepared by the methods of Example 16 and 17. Structure assignment was supported by the nmr spectrum and by elemental analysis.

Calcd. for $C_{13}H_{17}N_3O.3/8H_2O$: C, 65.59; H, 7.52; N, 17.65. Found: C, 65.75; H, 7.34; N, 17.89.

EXAMPLE 34

N,3-Dimethyl-4-phthalimidoaniline, Method A

To a stirred solution of 1.4 g of the product aniline of Example 31 and 2.5 ml of 37% aqueous formaldehyde in 19 ml of acetonitrile was added in portions 0.62 g of sodium cyanoborohydride. After twenty minutes the solution was adjusted to pH 7 with glacial acetic acid and stirred for another hour. Ice was added, acetonitrile was removed in vacuo, and the mixture was partitioned between water and dichloromethane. The organic layer was dried over potassium carbonate, filtered, and concentrated to an oil which was chromatographed on a silica gel column using dichloromethane as eluent. Fractions containing the title compound were concentrated to give a solid, m.p. 159°–161°. Structure assignment was supported by the nmr spectrum and by elemental analysis.

Calcd. for $C_{16}H_{14}N_2O_2$: C, 72.17; H, 5.30; N, 10.52. Found: C, 72.07; H, 5.16; N, 10.46.

EXAMPLE 35

N,N,3-Trimethyl-4-phthalimidoaniline, Method A

The chromatographic separation of Example 34 also afforded fractions containing the trimethyl compound as a solid, m.p. 196°–199°. Structure assignment was supported by the nmr spectrum and by elemental analysis.

Calcd. for $C_{17}H_{16}N_2O_2$: C, 72.84; H, 5.75; N, 9.99. Found: C, 73.00; H, 5.70; N, 10.00.

EXAMPLE 36

N,3-Dimethyl-4-phthalimidoaniline, Method B

To a mixture of the product aniline of Example 31 (15 g) and 18 g of anhydrous potassium carbonate suspended in 400 ml of dimethylformamide was added 11 g of methyl iodide in 30 ml of dimethylformamide. After 16 hours the mixture was concentrated to an oily residue which solidified upon trituration with water. The crude solid was purified by chromatography as in Example 34 to give the title compound. Samples prepared by the methods of Examples 34 and 36 were identical.

EXAMPLE 37

N,N,3-Trimethyl-4-phthalimidoaniline, Method B

The chromatographic separation of Example 36 afforded the title compound. Samples prepared by the methods of Examples 35 and 37 were identical.

EXAMPLE 38

2-Methyl-4-(N-methylacetamido)aniline

To 7.5 g of the product compound of Example 36 in 190 ml of pyridine cooled to 0° was added 13.5 ml of acetic anhydride. The solution was then allowed to stand at room temperature for 16 hours, after which time volatiles were removed in vacuo. The residue was partitioned between water and dichloromethane, and the organic phase was separated, dried over potassium carbonate, and concentrated to dryness. A portion (0.86 g) of the intermediate product was stirred at reflux in 20 ml of ethanol to which was added 0.54 ml of hydrazine hydrate. After one hour the mixture was concentrated in vacuo, and the residue was triturated with dichloromethane and filtered. The filtrate was concentrated to dryness, giving the title compound. Structure assignment was supported by the nmr spectrum.

EXAMPLE 39

2-[(2-Methyl-4-(N-methylacetamido)phenyl)amino]-1-pyrroline, hydrochloride

A mixture of 2-chloro-1-pyrroline, prepared as in Example 1 using toluene instead of acetonitrile, and 0.8 g of the product aniline of Example 38 in anhydrous toluene was heated at reflux for five hours. Upon cooling the toluene was removed by decanting and the residue was partitioned between water and dichloromethane. The aqueous layer was made alkaline with 50% sodium hydroxide and extracted with dichloromethane. The organic phase was dried over potassium carbonate, filtered, concentrated to an oil. The crude product was purified by low-pressure chromatography on silica gel, using as eluent 74:25:1 dichloromethane/ethanol/concentrated aqueous ammonia. The oily product was dissolved in ethanol and acidified with HCl in isopropyl alcohol. Addition of diethyl ether produced the title compound as the hydrochloride salt, m.p. 367°–370°. Structure assignment was supported by the nmr spectrum and by elemental analysis.

Calcd. for $C_{14}H_{19}N_3O·HCl$: C, 59.67; H, 7.15; N, 14.91; Cl, 12.58. Found: C, 59.30; H, 7.09; N, 14.80; Cl, 12.52.

EXAMPLE 40

2-Methyl-4-[N-methyl-N-(ethoxycarbonyl)amino]-aniline

The title compound was prepared by the method of Example 38 using 6 g of the product compound of Example 36 and 11 ml of ethyl chloroformate. Structure assignment was supported by the nmr spectrum.

EXAMPLE 41

2-[(2-Methyl-4-(N-methyl-N-(ethoxycarbonyl)-amino)-phenyl)amino]-1-pyrroline, hydrochloride The title compound was prepared by the method of Example 39 using 4.1 g of the products aniline of Example 40. Eluent for the chromatographic separation was 84.25:15:0.75 toluene/ethanol/ammonia. The hydrochloride salt was prepared in the same manner. Structure assignment was supported by the nmr spectrum and by elemental analysis.

Calcd. for $C_{15}H_{21}N_3O_2·HCl$: C, 57.78; H, 7.11; N, 13.48; Cl, 11.37. Found: C, 57.58; H, 7.03; N, 13.30; Cl, 11.21.

EXAMPLE 42

2-[(2-Methyl-4-(dimethylamino)phenyl)amino]-1-pyrroline, dihydrochloride. Method A A mixture of 1 g of the product aniline of Example 9, 0.6 g of 50% aqueous sodium hydroxide, 0.80 ml of 37% aqueous formaldehyde, and 1.0 g of 10% palladium on carbon was hydrogenated at 55 psi at room temperature until the theoretical uptake of hydrogen gas had been absorbed. The mixture was filtered and the filtrate was concentrated in vacuo. The free base was converted to the hydrochloride, m.p. 184°–186°, by the method included in Example 39. Structure assignment of the title compound was supported by the nmr spectrum and by elemental analysis.

Calcd. for $C_{13}H_{19}N_3·2HCl·1/4H_2O$: C, 52.98; H, 7.34; N, 14.26; Cl, 24.06. Found: C, 52.89; H, 7.24; N, 14.32; Cl, 23.95.

EXAMPLE 43

2-[(2-Methyl-4-(dimethylamino)phenyl)amino]-1-pyrroline, dihydrochloride, Method B To a mixture of 3.3 g of the product aniline of Example 9, 6.4 ml of 37% aqueous formaldehyde, and 2.5 ml of glacial acetic acid in 20 ml of acetonitrile was added 1.6 g of sodium cyanoborohydride. When addition was completed another 1.5 ml of acetic acid was added and the mixture was stirred for thirty minutes. The reaction mixture was poured onto ice, made alkaline with 50% aqueous sodium hydroxide, and extracted into dichloromethane. The organic layer was dried over potassium carbonate, filtered, and concentrated to an oil. The crude product was purified by column chromatography and the resultant oil was converted to the hydrochloride salt as in Example 42. Samples of the product prepared by the methods of Examples 42 and 43 were identical.

EXAMPLE 44

2-[(2-Methyl-4-(dimethylamino)phenyl)amino]-1-pyrroline, dihydrochloride, Method C The phthalimide protecting group of the product compound of Example 37 is removed using the method described in Example 32. The intermediate aniline is converted to the title compound using the method of Example 39.

EXAMPLE 45

2-[(2-Methyl-3-aminophenyl)amino]-1-pyrroline, dihydrochloride

The title compound (20.9 g) was prepared by the methods of Examples 8 and 9 using 2-chloro-1-pyrroline, prepared as in Example 1, and 30.0 g of 2-methyl-3-nitroaniline. Structure assignment was supported by the nmr spectrum and by elemental analysis.

Calcd. for $C_{11}H_{15}N_3·2HCl·5/8H_2O$: C, 48.32; H, 6.72; N, 15.36; Cl, 25.93. Found: C, 48.44; H, 6.96; N, 15.23; Cl, 25.70.

EXAMPLE 46

2-[(2-Methyl-3-acetamidophenyl)amino]-1-pyrroline, hydrochloride

The title compound (2.5 g) was prepared by the method of Example 17 using acetic anhydride and 3.0 g of the product aniline of Example 45. Structure assignment was supported by the nmr spectrum and by elemental analysis.

Calcd. for $C_{13}H_{17}N_3O·HCl·1/8H_2O$: C, 57.82; H, 6.82; N, 15.56; Cl, 13.13. Found: C, 57.74; H, 6.79; N, 15.64; Cl, 13.50.

EXAMPLE 47

2-[(2-Methyl-3-(ethoxycarbonylamino)phenyl)-amino]-1-pyrroline, hydrochloride

The title compound (2.2 g) was prepared by the method of Example 23 using ethyl chloroformate and 3.0 g of the product aniline of Example 45. Structure assignment was supported by the nmr spectrum and by elemental analysis.

Calcd. for $C_{14}H_{19}N_3O_2·HCl·1/8H_2O$: C, 56.05; H, 6.81; N, 14.01; Cl, 11.82. Found: C, 55.75; H, 6.76; N, 13.99; Cl, 12.03.

EXAMPLE 48

The following table lists representative results of the Cholera and Castor oil test (where done) for the previously described compounds useful in the method aspect of the invention and the novel compounds of the invention.

| Compound | Cholera $ID_{50}(mg/kg)$* | Castor Oil $ID_{50}(mg/kg)$-4 hr. |
| --- | --- | --- |
| Example 9 | 1.8/1.24 | 0.97 |
| Example 11 | 8.0/13.1 | 13.6 |
| Example 13 | 5.6/8.8 | |

CHART E -continued

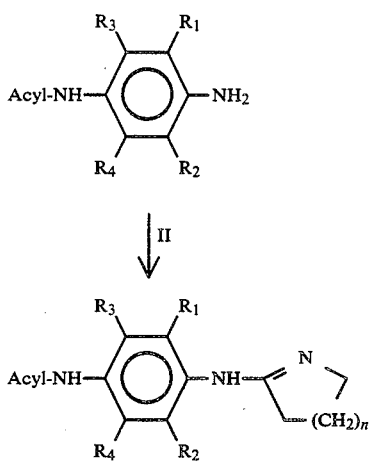

CHART F

XXI

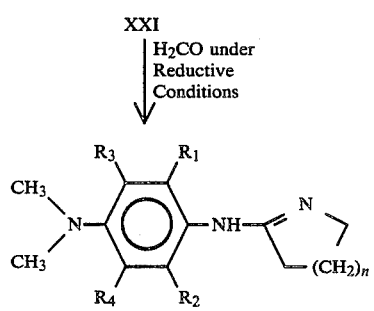

CHART G

XLIII

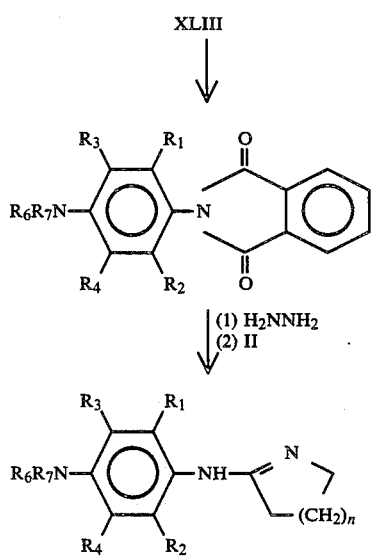

CHART H

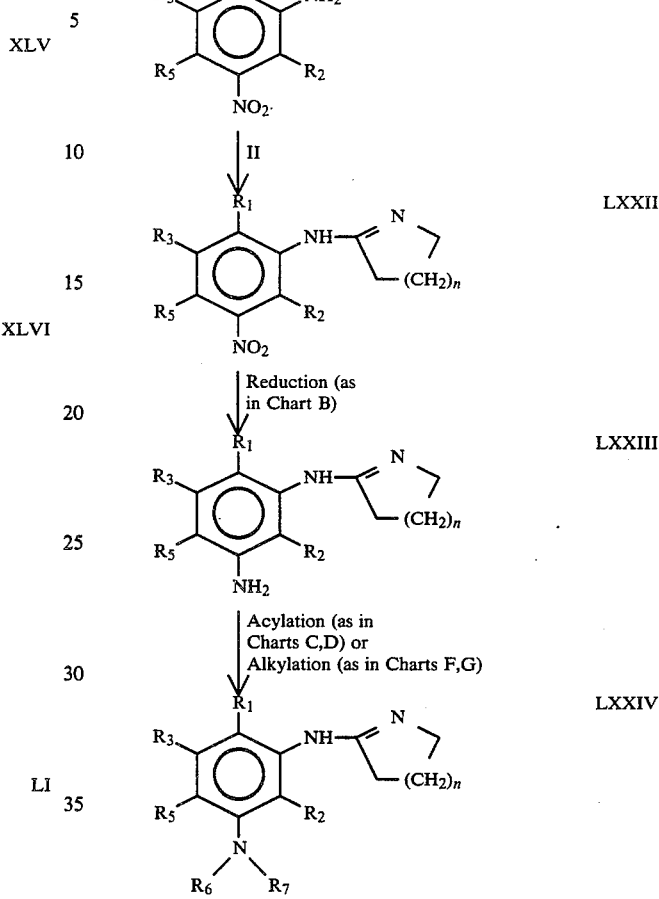

We claim:
1. A compound of the formula:

LXI
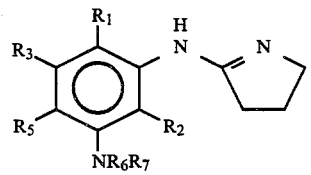

wherein $R_1$, $R_2$, $R_3$, and $R_5$, each being the same or different, are:
  (a) hydrogen;
  (b) alkyl of 1 to 6 carbon atoms, inclusive; or
  (c) halogen;
with the proviso that $R_1$ and $R_2$ are not hydrogen at the same time;
wherein $R_6$ and $R_7$, each being the same or different, are:
  (a) hydrogen;
  (b) alkyl of 1 to 6 carbon atoms, inclusive;
  (c) alkoxycarbonyl of 2 to 7 carbon atoms, inclusive;
  (d) aryloxycarbonyl of 6 to 12 carbon atoms, inclusive;
  (e) alkylcarbonyl of 2 to 7 carbon atoms, inclusive;
  (f) arylcarbonyl of 6 to 12 carbon atoms, inclusive;
  (g) hydroxyalkoxycarbonyl of 3 to 7 carbon atoms, inclusive;
  (h) haloalkylcarbonyl of 2 to 7 carbon atoms, inclusive; or the pharmaceutically acceptable salts; the compound being either hydrated or unhydrated
2. 2-[(2-Methyl-3-aminophenyl)amino]-1-pyrroline, dihydrochloride, a compound according to claim 1.
3. 2-[(2-Methyl-3-acetamidophenyl)amino]-1-pyrroline, hydrochloride, a compound according to claim 1.
4. 2-[(2-Methyl-3-(ethoxycarbonylamino)phenyl)amino]-1-pyrroline, hydrochloride, a compound according to claim 1.

* * * * *